United States Patent
Lee

(10) Patent No.: US 9,358,210 B2
(45) Date of Patent: Jun. 7, 2016

(54) SUSTAINED-RELEASE PELLETS CONTAINING TACROLIMUS AS AN ACTIVE INGREDIENT

(76) Inventor: Hee-Yub Lee, Suwon-si (KR)

( * ) Notice: Subject to any disclaimer, the term of this patent is extended or adjusted under 35 U.S.C. 154(b) by 305 days.

(21) Appl. No.: 13/879,657

(22) PCT Filed: Oct. 17, 2011

(86) PCT No.: PCT/KR2011/007708
§ 371 (c)(1),
(2), (4) Date: May 6, 2013

(87) PCT Pub. No.: WO2012/053785
PCT Pub. Date: Apr. 26, 2012

(65) Prior Publication Data
US 2013/0216624 A1    Aug. 22, 2013

(30) Foreign Application Priority Data
Oct. 19, 2010  (KR) .......... 10-2010-0101778

(51) Int. Cl.
*A61K 9/50* (2006.01)
*A61K 9/14* (2006.01)
*A61K 31/436* (2006.01)
*A61K 9/16* (2006.01)

(52) U.S. Cl.
CPC ............ *A61K 9/14* (2013.01); *A61K 9/1676* (2013.01); *A61K 31/436* (2013.01); *A61K 9/5078* (2013.01)

(58) Field of Classification Search
CPC ..... A61K 9/14; A61K 9/1676; A61K 9/5078; A61K 31/436
See application file for complete search history.

(56) References Cited

U.S. PATENT DOCUMENTS

| 4,916,138 | A | * | 4/1990 | Ueda et al. ............. 514/294 |
| 5,395,626 | A | * | 3/1995 | Kotwal et al. ............. 424/472 |
| 2008/0181947 | A1 | | 7/2008 | Kojima |
| 2009/0011018 | A1 | | 1/2009 | Kondo |
| 2010/0086592 | A1 | | 4/2010 | Singh |

FOREIGN PATENT DOCUMENTS

| KR | 10-0539706 | 12/2005 |
| KR | 10-2010-0060766 | 6/2010 |

OTHER PUBLICATIONS

Anonymous. 2009. Immune Suppressants. Murli Krishna Pharma Pvt. Ltd. [online]; downloaded from <URL: http://www.mkppl.com/immune_suppressants.html> on May 13, 2015; 1 page.*

* cited by examiner

*Primary Examiner* — Johann R Richter
*Assistant Examiner* — David Browe
(74) *Attorney, Agent, or Firm* — Lex IP Meister, PLLC

(57) ABSTRACT

The present invention relates to sustained-release pellets containing tacrolimus as an active ingredient. The sustained-release pellets of the present invention have multiple layers of hydroxypropyl methylcellulose, and may control the release of drugs by specific contents of hydroxypropyl methylcellulose and Surelease™, thus rendering the dissolution rate thereof uniform and stable, and enabling the dissolution rate to be adjusted as desired. The entire process for preparing the pellets of the present invention is carried out in a single fluidized-bed granulator, and therefore the preparation process is simplified and the time required for preparation is shortened while obtaining sustained-release pellets having uniform particle size distribution and contents. The sustained-release pellets of the present invention may have medicinal effects that last up to 24 hours, and therefore may be administered just once a day, thus improving patient compliance. Therefore, the pellets of the present invention may be effectively used in an orally administered pellet formulation containing tacrolimus as an active ingredient.

6 Claims, 3 Drawing Sheets

SUSTAINED-RELEASE PELLETS CONTAINING TACROLIMUS AS AN ACTIVE INGREDIENT

TECHNICAL FIELD

The present invention relates to sustained-release pellets containing tacrolimus as an active ingredient.

TECHNICAL ART

Tacrolimus was separated from the cell culture of streptomyces tsukubaensis, a kind of bacteria first discovered in Japan in 1980s and similar to fungi, and was initially used as immunosuppressant for organ transplant patients as orally administered formulation. It is a lactone compound and Macrolides drug with molecular weight 882.05 known as 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0]octacos-18-ene-2,3,10,16-tetraone, FK506 (See chemical formula 1).

[Chemical formula 1]

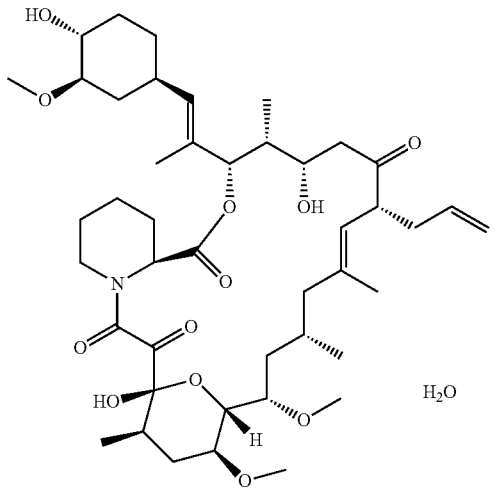

The said tacrolimus has been developed as transplant rejection inhibitor (Prograf™) for organ transplant patients, and in 1990s as ointment formulation to be first introduced for the treatment of atopic dermatitis and has been commercialized to atopic eczema treatment Protopic™, and later the purpose was extended to the treatment of other inflammatory skin diseases.

However, tacrolimus has the problem of low bioavailability and shortcoming of fluctuation depending on individuals, due to insufficient absorption into the blood because its solubility in water is very low at 1-2 ug/ml, preventing rapid drug release due to low dissolution rate when administered orally.

Therefore, a method is disclosed in Korean Patent No. 10-0092145 to increase the bioavailability of tacrolimus, which is dissolving it in an organic solvent, suspending hydroxypropyl methylcellulose in the solution, degassing the organic solvent, followed by drying, crushing and preparing solid dispersions. However, the said preparation method has the disadvantage that the manufacturing processes, such as drying, take a long time.

In addition WO 1995/001785 presents orally administered pharmaceutical compositions using a combination of polyglycerol fatty acid ester or Sorbitan fatty acid ester as a solubilizing agent, lipophilic diluting agent, and non-ionic surfactant, in order to increase the solubility of the sparingly water-soluble active substances, but it also has disadvantage that can cause irritation on the gastrointestinal tract.

Furthermore, Korean Patent No. 10-0440553 discloses a composition and preparation method of it by dissolving it in ethyl cellulose, mixing with hydroxypropyl methylcellulose and lactose, drying and spheronizing and mixing with magnesium stearate, in order to control the sustained-release of tacrolimus, there is a problem that it has to use a vacuum dryer for the formation of granules, that it needs special working conditions such as formation of the homogeneous particles by crushing by a mill for the formation of the powder particle with set width of particle diameter distribution, and that it cannot release a part due to a combination of ethyl cellulose.

To improve the problem of a tablet or capsule formulation, incidence of side effects such as the irregular rise in the plasma concentration and gastrointestinal irritation, therefore, there is a need to develop formulations, which have the equivalent effect to orally administered formulation, have uniform and stable dissolution rate, and contain tacrolimus that is a representative immunosuppressant currently on the market as an active ingredient, by controlling the release of drug in the desired form with constant release rate, reducing the variation between formulations, simplifying the composition.

Therefore, the inventors started the research to solve the above-mentioned problems of the conventional technology. While they were in research, they attempted to form the release control layer in multiple layers in the core, and put in the drug in the core layer and the outermost layer in order to control the release of drugs, and were able to obtain the sustained-release pellets with resolution rate that is uniform, stable and adjustable as desired. The entire process for preparing the pellets of the present invention is carried out in a single fluidized-bed coater, and thereof the preparation process is simplified and the time required for preparation is shortened while obtaining sustained-release pellets having uniform particle size distribution and contents. After conforming they were able to obtain the above sustained-release pellets, they completed the present invention.

DISCLOSURE OF INVENTION

Technical Problem

The purpose of the present is to provide orally administered sustained-release pellets containing tacrolimus with uniform dissolution rate as an active ingredient by controlling the release of drug.

Technical Solution

In order to achieve the above object, the present invention provides sustained-release pellets characterized by containing,
  pharmacological active ingredient layer (B1) containing tacrolimus as a main component around the center of the core (A), and hydroxypropyl methylcellulose as a binder;
  primary pharmacological inactive ingredient layer (C1) surrounding the said pharmacological active ingredient layer and containing hydroxypropyl methylcellulose;
  the sustained-release layer (D) surrounding the said primary pharmacological inactive ingredient layer, and containing aqueous ethylcellulose dispersion containing ammonium hydroxide, oleic acid and hypromellsoe (Surelease™ (SURELEASE NG-E-7-19050); Colorcon, Inc., West Point, Pa. U.S.A.) and hydroxypropyl methylcellulose;

the secondary pharmacological inactive ingredient layer (C2) surrounding the said sustained-release layer, and containing hydroxypropyl methylcellulose; and initial release membrane layer (B2) surrounding the said secondary pharmacological inactive ingredient layer and containing tacrolimus and hydroxypropyl methylcellulose;

the ratio of tacrolimus:hydroxypropyl methylcellulose: Surelease™ in the said pellets of 1:10~15:3.6~4.8.

Advantageous Effects

The sustained-release pellets of the present invention have multiple layers of hydroxypropyl methylcellulose, and may control the release of drugs by specific contents of hydroxypropyl methylcellulose and Surelease™, thus rendering the dissolution rate thereof uniform and stable, and enabling the dissolution rate to be adjusted as desired. The entire process for preparing the pellets of the present invention is carried out in a single fluidized-bed coater, and thereof the preparation process is simplified and the time required for preparation is shortened while obtaining sustained-release pellets having uniform particle size distribution and contents. The sustained-release pellets of the present invention may have medicinal effects that last up to 24 hours, and therefore may be administered just once a day, thus improving patient compliance. Therefore, the pellets of the present invention may be effectively used in an orally administered pellet formulation containing tacrolimus as an active ingredient

BRIEF DESCRIPTION ON THE DRAWINGS

BEST MODE FOR CARRYING OUT THE INVENTION

Figure 1:
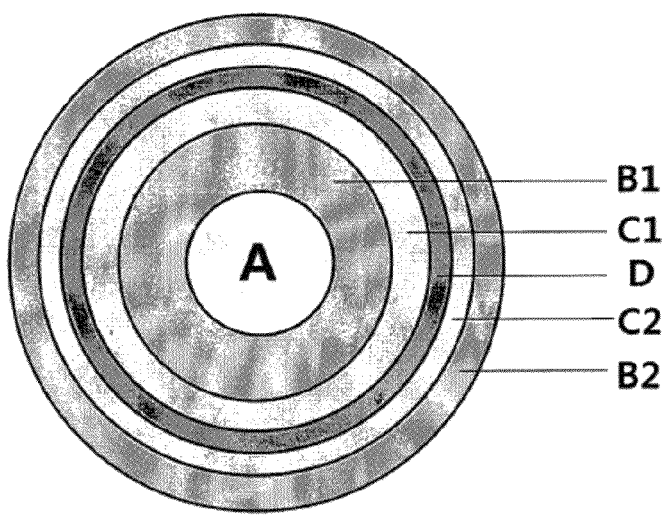
FIG. 1 is a schematic view of the pellet according to the present invention.

Hereinafter, the present invention is described in detail.

The present invention provides sustained-release pellets characterized by containing tacrolimus as effective ingredient and, pharmacological active ingredient layer (B1) containing tacrolimus as a main component around the center of the core (A), and hydroxypropyl methylcellulose as a binder;

primary pharmacological inactive ingredient layer (C1) surrounding the said pharmacological active ingredient layer and containing hydroxypropyl methylcellulose;

the sustained-release layer (D) surrounding the said primary pharmacological inactive ingredient layer, and containing Surelease™ and hydroxypropyl methylcellulose;

the secondary pharmacological inactive ingredient layer (C2) surrounding the said sustained-release layer, and containing hydroxypropyl methylcellulose; and coated initial release membrane layer (B2) surrounding the said secondary pharmacological inactive ingredient layer and containing tacrolimus and hydroxypropyl methylcellulose.

Hereinafter, each configuration is described in detail.

In the sustained-release pellets according to the present invention, any known core material can be used without restrictions as the said core (A). For example, granular white sugar, sugar, dicalcium phosphate, dehydrate (Di-tab™, Rhodia), microcrystalline cellulose (Vivapur™, JRS Pharma), etc. can be used, but are not limited thereto.

In a sustained-release pellet according to the present invention, the said core is preferably 75~85 wt % of the pellet.

In sustained-release pellets according to the present invention, the said pharmacological active ingredient layer (B1) surrounds in the form mixed with the drug and binder, preferably 0.5~1.5 wt % of tacrolimus as the drug and 5.0~7.0 wt % of hydroxypropyl methylcellulose as the binder.

In sustained-release pellets according to the present invention, the said pharmacological active ingredient layer may include more slip modifiers. Known common slip modifier with appropriate properties can be used for the said slip modifier. For example, silicon dioxide, colloidal silicon dioxide, fumed silicon dioxide, calcium silicate, magnesium carbonate, talc, calcium stearate, magnesium stearate, zinc stearate, stearowet C, magnesium lauryl sulfate, magnesium oxide, etc, preferably talc. The said slip modifier may be included in 0.5~0.9 wt % preferably.

In the sustained-release pellets according to the present invention, the said pharmacological inactive ingredient layers (C1 and C2) are coated between the pharmacological active layer (B1) or the initial release control membrane layer (B2), and the sustained-release layer (D) to prevent the inhibition of drug release caused by the combination of the layer that contains a drug (B1 or B2) and sustained-release layer (D) and to ensure smooth dissolution of the drug.

In order to achieve these objectives, it is desirable to use hydroxypropyl methylcellulose, preferably with content of 1.5~1.8 wt %, as the said pharmacological inactive ingredient layer.

In the sustained-release pellets according to the present invention, the said sustained-release layer (D) plays the role to control the drug release for slower dissolving of the drug. It is desirable that these sustained-release layers contain hydroxypropyl methylcellulose and Surelease™, preferably 3.6~4.8 wt % of Surelease™ and 0.3~0.6 wt % of hydroxypropyl methylcellulose. Surelease™ is prepared by blending ethylcellulose with oleic acid, then melted and extruded. The molten plasticized ethylcellulose is then directly emulsified in ammoniated water in a high shear mixing device under pressure. Ammonium oleate is formed in situ to stabilize and form the dispersion, Additional purified water is then added to achieve the final solids content.

In the sustained-release pellets according to the present invention, the said initial release control membrane layer (B2) releases the drug fast to let the drug reach the effective blood concentration in a short time.

The said initial release control membrane layer form the outermost layer mixed with the drug and binder, preferably 0.05~0.15 wt % of tacrolimus as the drug and 3.5~4.0 wt % of hydroxypropyl methylcellulose as the binder.

In the pellets of such form in accordance with the present invention, the wt % of tacrolimus:hydroxypropyl methylcellulose:solid Surelease™ of the said pellets is 0.6~1.65:10~15:3.6~4.8 respectively, and weight ratio is 1:10~15:3.6~4.8, more preferably 1:13.67:4.56.

When the ratio exceeds the said range, the release of the active ingredient is reduced to 17.8% in 30 min, 41.2% in 90 min, and 86.5% in 24 hrs, at the ratio of tacrolimus:hydroxypropyl methylcellulose:solid Surelease™ in the pellet=1:16.76:4.97; when the ratio is below the said range, the release of the active ingredient is reduced to 44.5% in 30 min, 82.4% in 90 min, and 89.9% in 24 hrs, at the ratio of tacrolimus:hydroxypropyl methylcellulose:solid Surelease™ in the pellet=1:9.71:3.52, so sustained-release effect is not expected.

In addition, the said sustained release pellet containing tacrolimus as an active ingredient is prepared in the following steps:
 (step 1) coating step of pharmacological active ingredient layer coating on the core;
 (step 2) coating step of the primary pharmacological inactive ingredient layer on the pharmacological active ingredient layer prepared in the said step 1;
 (step 3) coating step of the sustained-release layer on the primary pharmacological inactive ingredient layer prepared in the said step 2;
 (step 4) coating step of the secondary pharmacological inactive ingredient layer on the sustained-release layer prepared in the said step 3; and
 (step 5) coating step of the initial release control membrane layer on the secondary pharmacological inactive ingredient layer prepared in the said step 4.

Hereinafter, each step is described in detail.

First, said step 1 is the coating step of the pharmacological active ingredient layer on the core.

The said step 1 can be performed by putting 75~85 wt % of core in the fluidized-bed coater and spray-coating the solution of 0.5~1.5 wt % of tacrolimus and 5.0~7.0 wt % of hydroxypropyl methylcellulose dissolved in the solvent on the said core.

At this time, any pharmaceutically usable solvent capable of dissolving tacrolimus and hydroxypropyl methylcellulose can be used as the solvent, including ethanol, methylene chloride, isopropanol, purified water or a mixed solution of these.

In addition, a slip modifier may be added to the said pharmacological active ingredient layer by dissolving 0.5~0.9 wt % of the slip modifier with the said tacrolimus and hydroxypropyl methylcellulose in the solvent and spray coating it on the said core.

Next, the said step 2 is the coating step of the primary pharmacological inactive ingredient layer on the pharmacological active ingredient layer prepared in the said step 1.

The said step can be carried out by dissolving 1.5~1.8 wt % of the hydroxypropyl methylcellulose in the solvent and spray coating the solution on the pharmacological active ingredient layer prepared by the said step 1 in the fluidized-bed coater.

At this time, any pharmaceutically usable solvent capable of dissolving tacrolimus and hydroxypropyl methylcellulose can be used as the solvent, including ethanol, methylene chloride, isopropanol, purified water or a mixed solution of these.

Next, the step 3 is the sustained-release layer on the primary pharmacological inactive ingredient layer prepared in the said step 2.

The said step can be carried out by dissolving 0.3~0.6 wt % of the hydroxypropyl methylcellulose and 3.6~4.8 wt % of the solid Surelease™ in the solvent and spray coating the solution on the primary pharmacological inactive ingredient layer prepared by the said step 2 in the fluidized-bed coater.

At this time, any pharmaceutically usable solvent capable of dissolving tacrolimus, hydroxypropyl methylcellulose and the solid Surelease™ can be used as the solvent, including ethanol, methylene chloride, isopropanol, purified water or a mixed solution of these.

Next, the step 4 is the coating step of secondary pharmacological inactive ingredient layer on the sustained-release layer prepared in the said step 3.

The said step can be carried out by dissolving 1.5~1.8 wt % of the hydroxypropyl methylcellulose in the solvent and spray coating the solution on the sustained-release layer prepared by the said step 3 in the fluidized-bed coater.

At this time, any pharmaceutically usable solvent capable of dissolving tacrolimus and hydroxypropyl methylcellulose can be used as the solvent, including ethanol, methylene chloride, isopropanol, purified water or a mixed solution of these.

Next, the step 5 is the coating step of the initial release control membrane layer on the secondary pharmacological inactive ingredient layer prepared in the said step 4.

The said can be performed by dissolving 0.05~0.15 wt % of tacrolimus and 3.5~4.0 wt % of hydroxypropyl methylcellulose in the solvent and spray-coating the solution on the secondary pharmacological inactive ingredient layer prepared in the said step 4 in the fluidized-bed coater.

At this time, any pharmaceutically usable solvent capable of dissolving tacrolimus and hydroxypropyl methylcellulose can be used as the solvent, including ethanol, methylene chloride, isopropanol, purified water or a mixed solution of these.

Figure 2:
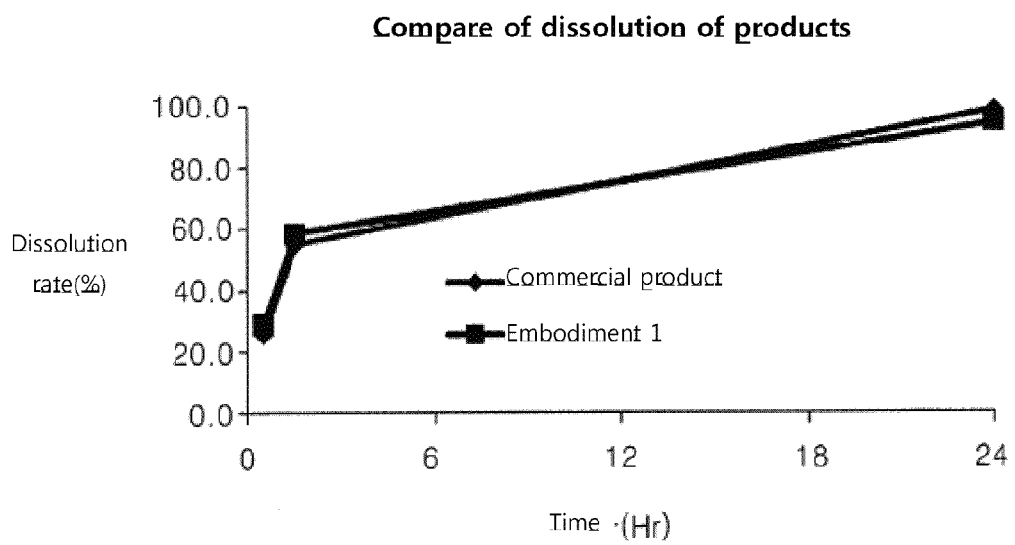
FIG. 2 is the graph comparing the dissolution rates of an embodiment pellet according to the present invention, and ADVAGRAF, a conventional commercially available product.
Figure 3:
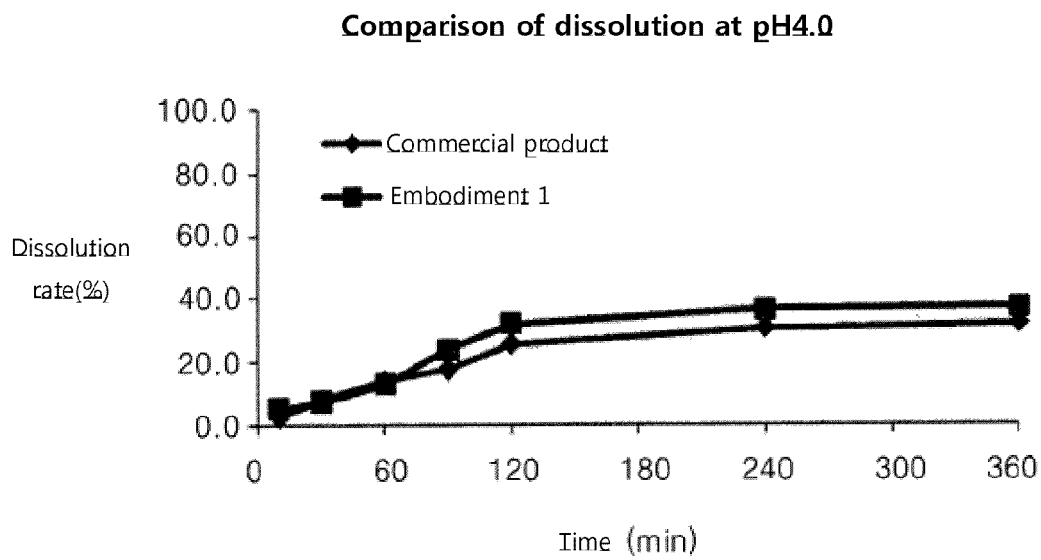
FIG. 3 is the graph comparing the dissolution rates at pH4.0 of an embodiment pellet according to the present invention, and ADVAGRAF, a conventional commercially available product.
Figure 4:
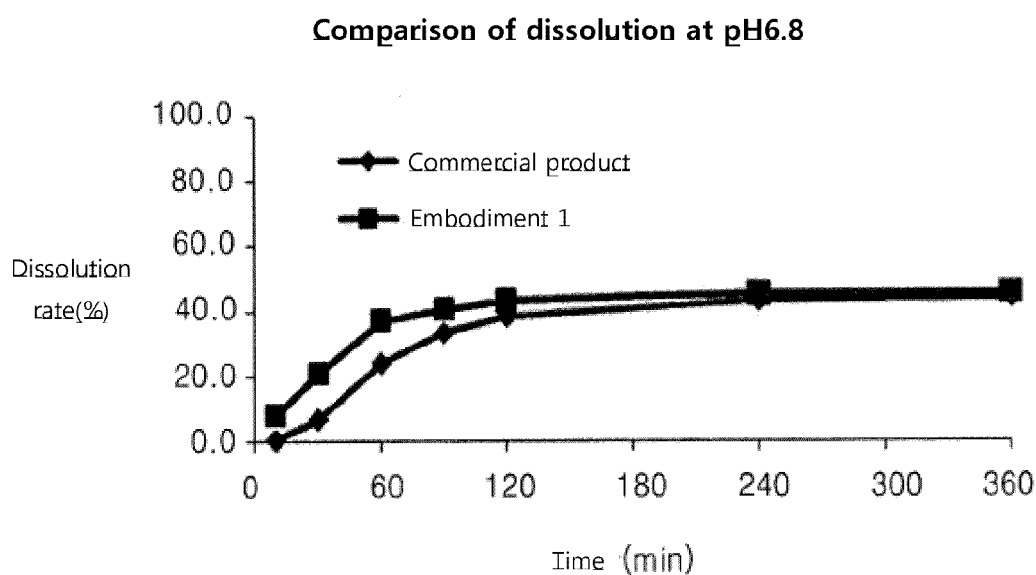
FIG. 4 is the graph comparing the dissolution rates at pH6.8 of an embodiment pellet according to the present invention, and ADVAGRAF, a conventional commercially available product.

As the result of the measure of the elution pattern of the sustained-release pellets of the present invention prepared by the said preparation method in the product elution test solution, it showed, as in FIG. 2, a fast increase in the dissolution rate till 60% within 1-2 hours in the equivalent pattern to ADVAGRAF, the commercial hard capsule formulation containing tacrolimus, followed by slower increase in the dissolution rate, releasing the drug for 24 hours; the comparison dissolution environment measure at pH 4.0 (stomach environment) and pH 6.8 (intestinal environment) showed, as in FIGS. 3 and 4, the dissolution pattern equivalent to ADVAGRAF, a formulation in the market.

Therefore, the sustained-release pellets of the present invention have multiple layers of hydroxypropyl methylcellulose, and may control the release of drugs by specific contents of hydroxypropyl methylcellulose and Surelease™, thus rendering the dissolution rate thereof uniform and stable, and enabling the dissolution rate to be adjusted as desired. The entire process for preparing the pellets of the present invention is carried out in a single fluidized-bed coater, and thereof the preparation process is simplified and the time required for preparation is shortened while obtaining sustained-release pellets having uniform particle size distribution and contents. The sustained-release pellets of the present invention may have medicinal effects that last up to 24 hours, and therefore may be administered just once a day, thus improving patient compliance. Therefore, the pellets of the present invention may be effectively used in an orally administered pellet formulation containing tacrolimus as an active ingredient.

BEST MODE FOR CARRYING OUT THE INVENTION

Hereinafter, the present invention is described in detail by the embodiment.

However, the following embodiment is only an example of the present invention, and the present invention is not limited to this embodiment below.

<Embodiment 1> Preparation of the Sustained-Release Pellets Containing Tacrolimus Step 1: Coating Step of Pharmacological Active Ingredient Layer on the Core.

Put and dissolve 0.9 g of tacrolimus, 6.26 g of hydroxypropyl methylcellulose and 0.84 g of talc in the mixture of 81 g of ethanol and 14 g of water to prepare water-soluble polymer composition containing main drug; put 79.043 g of 20 mesh-sugar spheres in the fluidized-bed coater, and coat it with the said water-soluble polymer composition containing the main drug in the condition of spraying speed of 5 g/min, air supply temperature of 58 C, drug temperature 52 C and spray pressure of 1.5 bar; to prepare a composition containing the water-soluble polymer layer containing 87.043 wt % of tacrolimus for the total.

Step 2: Coating Step of Primary Pharmacological Inactive Ingredient Layer 1.67 g hydroxypropyl methylcellulose was put in and dissolved in the mixture of 12.5 g of ethanol and 3.4 g of water; 1.67 wt % of this solution was coated on the surface of the pharmacological active ingredient layer prepared in said step 1, in the fluidized-bed coater.

Step 3: Coating Step of Sustained-Release Layer on the Primary Pharmacological Inactive Ingredient Layer 0.517 g of hydroxypropyl methylcellulose and 18.62 g of solid Surelease™ were put in and dissolved in the mixture of 3.4 g of ethanol and 12.17 g of water; 10.17 wt % of this solution was coated on the surface of the primary pharmacological inactive ingredient layer prepared in said step 2, in the fluidized-bed coater.

Step 4: Coating Step of the Secondary Pharmacological Inactive Ingredient Layer 1.67 g of hydroxypropyl methylcellulose was put in and dissolved in the mixture of 12.5 g of ethanol and 3.4 g of water; 1.67 wt % of this solution was coated on the surface of the sustained-release layer prepared in said step 3.

Step 5: Coating Step of the Initial Release Control Membrane Layer on the Secondary Pharmacological Inactive Ingredient Layer 0.12 g of tacrolimus and 3.825 g of hydroxypropyl methylcellulose were put in and dissolved in the mixture of 35 g of ethanol and 10 g of water; 4.445 wt % of this initial release controlled membrane layer coating solution containing the main drug on the surface of the secondary pharmacological inactive ingredient layer prepared in said step 4.

EXPERIMENTAL EXAMPLE 1

Comparison of the Dissolution Rate in the Product Dissolution Test Solution

In order to measure the dissolution rate of the Sustained-release pellets containing tacrolimus prepared in the said embodiment 1, 900 ml of 0.005% hydroxypropyl methylcellulose aqueous solution adjusted to pH 4.5 using phosphoric acid was used as the test solution; the dissolution test was carried out for 24 hours at 50 rpm in the second dissolution method of the Korean Pharmacopoeia.

The dissolution samples were tested for the dissolution rate for 30 min, 90 min, and 24 hrs respectively; the analysis of dissolution samples was carried out by analyzing the dissolved solution using HPLC.

An ultraviolet spectrophotometer (measurement wavelength: 230 nm) was used as the detector; Shiseido C8 (5 um, 150 mm×4.6 mm) column was used; the column temperature of 40 C and the flow rate of 1.0 ml/min were used for the test; a mixture of acetonitrile/water/methanol/diluted phosphoric acid at the ratio of 560/260/180/1 was used as the mobile phase; ADVAGRAF, an sustained-release capsule formulation containing tacrolimus as an active ingredient was used as the comparison group.

TABLE 1

| | Dissolution rate Dissolution rate (%) | |
| --- | --- | --- |
| Time | Embodiment 1 | ADVAGRAF |
| after 30 min | 29.0 | 26.2 |
| after 90 min | 58.6 | 55.5 |
| after 2 hrs | 94.4 | 98.1 |

As the result, the dissolution rate of the sustained-release pellets of the present invention containing tacrolimus showed, as in Table 1 and FIG. 2, 29.0% 30 minutes after the administration, 58.6% after 90 minutes, and 94.4% after 24 hours; it was found that the dissolution pattern was similar to that of ADVAGRAF, a sustained-release capsule formulation containing tacrolimus composition as an active ingredient.

Therefore, the sustained-release pellets of the present invention may be effectively used just once a day in an orally administered tacrolimus pellets since the dissolution rate is maintained constant in a similar pattern as the commercially available formulation pellets.

EXPERIMENTAL EXAMPLE 2

Comparison of the Dissolution Rate at pH 4.0

The dissolution rate was measured in the same way as the said experimental example 1, except that pH is 4.0 and the measurement time is 10, 30, 60, 90, 120, 240 and 360 minutes.

TABLE 2

| | Dissolution rate Dissolution rate (%) | |
| --- | --- | --- |
| Time | Embodiment 1 | ADVAGRAF |
| after 10 min | 5.0 | 2.6 |
| after 30 min | 7.3 | 7.7 |
| after 60 min | 12.9 | 13.8 |
| after 90 min | 23.7 | 17.5 |
| after 120 min | 31.9 | 25.5 |
| after 240 min | 36.3 | 30.4 |
| after 360 min | 37.2 | 31.7 |

As the result, the dissolution rate at pH4.0 of the sustained-release pellets of the present invention containing tacrolimus showed, as in Table 2 and FIG. 3, 5.0% 10 minutes after the administration, 7.3% after 30 minutes, 12.9% after 60 minutes, 23.7% after 90 minutes, 31.9% after 120 minutes, 36.3% after 240 minutes and 36.3% after 360 minutes; it was found that the dissolution pattern was similar to that of ADVAGRAF, a sustained-release capsule formulation containing tacrolimus composition as an active ingredient.

Therefore, the sustained-release pellets of the present invention may be effectively used in an orally administered tacrolimus pellets since the dissolution rate at pH4.0 is maintained constant at 40% in a similar pattern as the commercially available formulation pellets.

EXPERIMENTAL EXAMPLE 3

Comparison of the Dissolution Rate at pH 6.8

The dissolution rate was measured in the same way as the said experimental example 1, except that pH is 6.8 and the measurement time is 10, 30, 60, 90, 120, 240 and 360 minutes.

TABLE 3

| Time | Dissolution rate Dissolution rate (%) | |
|---|---|---|
| | Embodiment 1 | ADVAGRAF |
| after 10 min | 8.0 | 0.5 |
| after 30 min | 20.9 | 6.8 |
| after 60 min | 37.0 | 23.8 |
| after 90 min | 40.6 | 33.0 |
| after 120 min | 43.1 | 38.0 |
| after 240 min | 45.3 | 42.9 |
| after 360 min | 45.6 | 43.8 |

As the result, the dissolution rate at pH6.8 of the sustained-release pellets of the present invention containing tacrolimus showed, as in Table 3 and FIG. 4, 8.0% 10 minutes after the administration, 20.9% after 30 minutes, 37.0% after 60 minutes, 40.6% after 90 minutes, 43.1% after 120 minutes, 45.3% after 240 minutes and 45.6% after 360 minutes; it was found that the dissolution pattern was similar to that of ADVAGRAF, a sustained-release capsule formulation containing tacrolimus composition as an active ingredient.

Therefore, the sustained-release pellets of the present invention may be effectively used in an orally administered tacrolimus pellets since the dissolution rate at pH6.8 is maintained constant at 40% in a similar pattern as the commercially available formulation pellets.

COMPARATIVE EXAMPLE

Release Effects in Accordance with the Wt % Ratio, Tacrolimus:Hydroxypropyl Methylcellulose:Surelease™ in the Pellet The dissolution rate of the prepared pellets prepared in the same way as the embodiment 1 was measured in the same way as experimental example 1, except that (A) was prepared at the wt % ratio of tacrolimus:hydroxypropyl methylcellulose:Surelease™ in the pellets at 1:16.76:4.97 respectively and that (B) was prepared at the wt % ratio of tacrolimus:hydroxypropyl methylcellulose:Surelease™ in the pellets at 1:9.71:3.52 respectively.

TABLE 4

| Time | Dissolution rate Dissolution rate (%) | | |
|---|---|---|---|
| | Embodiment 1 | Comparative example 1 | Comparative example 2 |
| after 30 min | 29.0 | 17.8 | 44.5 |
| after 90 min | 58.6 | 41.2 | 82.4 |
| after 24 hrs | 94.4 | 86.5 | 89.9 |

Figure 5:
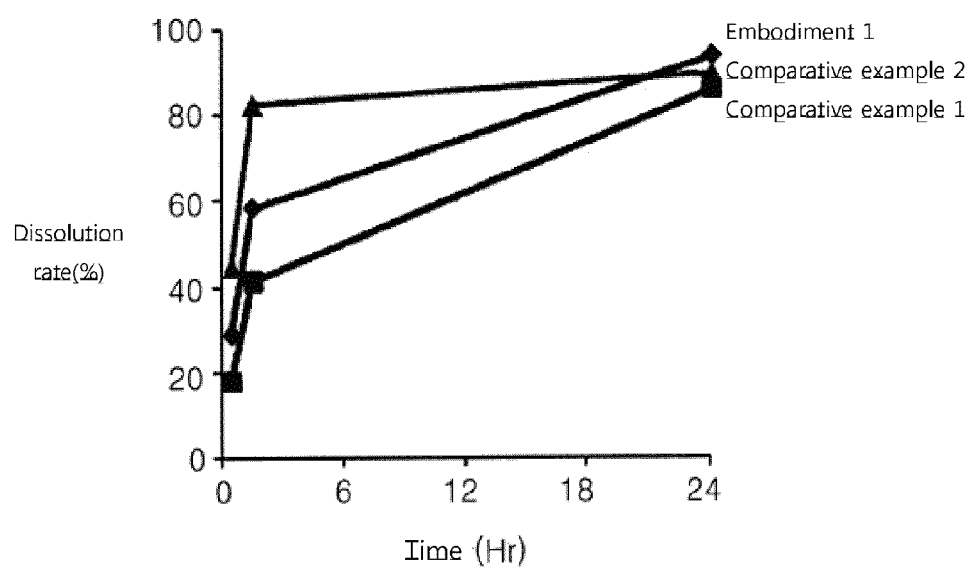
FIG. 5 is the graph comparing the dissolution rates according to the wt % of components of the pellet of the present invention.

As the result, the dissolution rate of the pellets of the present invention showed, as in Table 4 and FIG. 5, 29.0% 30 minutes after the administration, 58.6% after 90 minutes, and 94.4% after 24 hours, but the release of the active ingredient was reduced to 17.8% in 30 min, 41.2% in 90 min, and 86.5% in 24 hrs, at the weight ratio of tacrolimus:hydroxypropyl methylcellulose: Surelease™ in the pellet=1:16.76:4.97.

In addition, when the composition ratio is lower than the pellet containing tacrolimus of the present invention, sustained-release effect was reduced to 44.5% in 30 min, 82.4% in 90 min, and 89.9% in 24 hrs, at the ratio of tacrolimus:hydroxypropyl methylcellulose: Surelease™ in the pellet=1:9.71:3.52.

Therefore, the pellets of the present invention maybe effectively used in an orally administered sustained-release tacrolimus pellets because the release is degraded or the sustained-release effect cannot be expected when the weight ratio of tacrolimus: hydroxypropyl methylcellulose: Surelease™ is 1: 10~15:3.6~4.8, which is the presented weight ratio of the pellet of the present invention.

The invention claimed is:

1. Sustained-release pellets which contain tacrolimus as an active ingredient, the sustained-release pellets comprising:
   a pharmacologically active ingredient layer containing 0.5~1.5 wt % of tacrolimus as a main ingredient and 5.0~6.5 wt % of hydroxypropyl methylcellulose as a binder around a core;
   a primary pharmacologically inactive ingredient layer surrounding the pharmacologically active ingredient layer, and containing 1.5~1.7 wt % of hydroxypropyl methylcellulose;
   a sustained-release layer surrounding the primary pharmacologically inactive ingredient layer, and containing 3.6~4.8 wt % of aqueous ethylcellulose dispersion containing ammonium hydroxide, oleic acid and hypromellose (SURELEASE NG E-7-19050) and 0.3~0.6 wt % of hydroxypropyl methylcellulose;
   a secondary pharmacologically inactive ingredient layer surrounding the sustained-release layer, and containing 1.5~1.7 wt % of hydroxypropyl methylcellulose; and
   an initial release membrane layer surrounding the secondary pharmacologically inactive ingredient layer, and containing 0.10~0.15 wt % of tacrolimus and 3.5~4.0 wt % of hydroxypropyl methylcellulose.

2. The sustained-release pellets according to claim 1, wherein the ratio of tacrolimus:hydroxypropyl methylcellulose:aqueous ethylcellulose dispersion containing ammonium hydroxide, oleic acid and hypromellose in the pellets is 1:13.67:4.56.

3. The sustained-release pellets according to claim 1, wherein the core is selected from the group consisting of granular white sugar, sugar, dicalcium phosphate dihydrate and microcrystalline cellulose.

4. The sustained-release pellets according to claim 1, wherein the pharmacologically active ingredient layer further contains a slip modifier.

5. The sustained-release pellets according to claim 4, wherein the slip modifier is selected from the group consisting of silicon dioxide, colloidal silicon dioxide, fumed silicon dioxide, calcium silicate, magnesium carbonate, talc, calcium stearate, magnesium stearate, zinc stearate, stearowet C, magnesium lauryl sulfate and magnesium oxide.

6. The sustained-release pellets according to claim 4, wherein the pharmacologically active ingredient layer contains 0.5~0.9 wt % of the slip modifier.

* * * * *